US00PP12831P2

(12) United States Plant Patent
Kievit

(10) Patent No.: US PP12,831 P2
(45) Date of Patent: Aug. 6, 2002

(54) FUCHSIA PLANT NAMED 'KIEWIDIV'

(75) Inventor: Christa Kievit, Hem-Venhuizen (NL)

(73) Assignee: Kieft Seed Holland, Venhuizen (NL)

( * ) Notice: Subject to any disclaimer, the term of this patent is extended or adjusted under 35 U.S.C. 154(b) by 36 days.

(21) Appl. No.: 09/795,459

(22) Filed: Mar. 1, 2001

(51) Int. Cl.[7] ..... A01H 5/00
(52) U.S. Cl. ..... Plt./300
(58) Field of Search ..... Plt./300

(56) References Cited

PUBLICATIONS

GTITM UPOVROM Citation for 'Kiewidiv' as per NL PBR FSA0010; Oct. 22, 1999.*

* cited by examiner

*Primary Examiner*—Kent L. Bell
(74) *Attorney, Agent, or Firm*—C. A. Whealy

(57) ABSTRACT

A new and distinct cultivar of Fuchsia plant named 'Kiewidiv', characterized by its numerous red and white bi-colored flowers; upright plant habit; and freely branching growth habit.

1 Drawing Sheet

BACKGROUND OF THE INVENTION

The present invention relates to a new and distinct cultivar of Fuchsia plant, botanically known as *Fuchsia×hybrida*, and hereinafter referred to by the name 'Kiewidiv'.

The new Fuchsia is a product of a planned breeding program conducted by the Inventor in Venhuizen, The Netherlands. The objective of the breeding program was to create new Fuchsia cultivars with compact plant habit and numerous attractive flowers.

The new Fuchsia originated from a cross made by the Inventor of two proprietary selections of *Fuchsia×hybrida*, not patented. The cultivar 'Kiewidiv' was discovered and selected by the Inventor as a flowering plant within the progeny of the stated cross in a controlled environment in Venhuizen, The Netherlands. Plants of the new Fuchsia differ from plants of the parent selections primarily in flower color.

Asexual reproduction of the new Fuchsia by terminal cuttings taken at Venhuizen, The Netherlands, since 1997 has shown that the unique features of this new Fuchsia are stable and reproduced true to type in successive generations.

BRIEF SUMMARY OF THE INVENTION

The cultivar 'Kiewidiv' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Kiewidiv'. These characteristics in combination distinguish 'Kiewidiv' as a new and distinct cultivar:

1. Numerous red and white bi-colored flowers.
2. Upright plant habit.
3. Freely branching growth habit.

BRIEF DESCRIPTION OF THE PHOTOGRAPH

The accompanying colored photograph illustrates the overall appearance of the new Fuchsia, showing the colors as true as it is reasonably possible to obtain in colored reproductions of this type. Colors in the photograph may differ slightly from the color values cited in the detailed botanical description which accurately describe the colors of the new Fuchsia. The photograph comprises a side perspective view of a typical potted plant of 'Kiewidiv'.

DETAILED BOTANICAL DESCRIPTION

In the following description, color references are made to The Royal Horticultural Society Colour Chart except where general terms of ordinary dictionary significance are used. Plants used for the description were grown during the spring in Venhuizen, The Netherlands, in a glass-covered greenhouse. During the production of the plants, the following measurements were recorded: day temperatures ranging from 18 to 20° C.; night temperatures ranging from 15 to 18° C.; and light levels about 40,000 lux. Rooted cuttings were planted in 12.5-cm containers and were pinched about 2 to 3 weeks later. The botanical description was taken about 60 to 80 days after planting.

Botanical classification: *Fuchsia×hybrida* cultivar 'Kiewidiv'.

Parentage:

*Female or seed parent.*—Proprietary selection of *Fuchsia×hybrida*, not patented.

*Male, or pollen, parent.*—Proprietary selection of *Fuchsia×hybrida*, not patented.

Propagation:

*Type cutting.*—Terminal cuttings.

*Time to initiate roots.*—About 10 to 14 days at 18 to 21° C.

*Time to produce a rooted cutting.*—About 21 to 28 days at 18 to 21° C.

*Root description.*—Fine, fibrous and freely-branching.

Plant description:

*Form.*—Upright and uniform plant habit, relatively compact, and freely branching, bushy. Freely flowering. Appropriate for 10 to 12.5-cm containers. Rapid growth rate.

*Plant height at flowering.*—About 20 to 25 cm.

*Plant diameter at flowering.*—About 22.5 cm.

*Branching habit.*—Freely branching; typically 10 to 15 lateral branches develop per plant. Pinching (removal of terminal apex) enhances lateral branch development.

*Lateral branch description.*—Length: About 10 to 15 cm. Internode length: About 2 to 3 cm. Aspect: Erect. Strength: Moderately strong. Texture: Smooth, pubescent. Color: Close to 59A to 59B.

*Foliage description.*—Leaves simple, opposite, generally symmetrical. Length: About 3 to 5 cm. Width: About 1.5 to 1.75 cm. Shape: Ovate, elongate. Apex: Acute. Base: Obtuse. Margin: Entire. Texture: Smooth, glabrous. Petiole length: About 1.5 cm. Color: Young and mature foliage, upper surface: 146A. Young and mature foliage, lower surface: 146C.

Flower description:

*Flower type and habit.*—Single bi-colored axillary flowers. Freely flowering; potentially one or two flowers per every axil. Flowering recurrent. Flowers not persistent. Flowers not fragrant.

*Natural flowering season.*—April through October in northern Europe.

*Flower longevity.*—Flowers last about 2 to 3 days on the plant.

*Flower orientation.*—Initially upright, to pendulous.

*Flower diameter.*—About 4 cm.

*Flower height.*—About 4.5 cm.

*Flower buds.*—Shape: Oblong. Length: About 3 cm. Width: About 8 to 12 mm. Color: 45A.

*Petals.*—Quantity: Four, overlapping. Length: About 2.5 to 3 cm. Width: About 8 mm. Shape: Cordate. Apex: Emarginate. Margin: Entire. Texture: Glabrous, smooth and velvety. Color: When opening and fully opened, upper surface: 155D, with red, close to 45A, veins. When opening and fully opened, lower surface: 155D, with red, close to 45A, veins.

*Sepals.*—Quantity: Four, fused at base. Length: About 2 cm. Width: About 6 mm. Aspect: Incurved to flat. Shape: Elongated oblong. Apex: Acute. Margin: Entire. Texture: Glabrous, smooth, velvety. Color: When opening and fully opened, upper surface: 45A. When opening and fully opened, lower surface: 45A to 45B.

*Peduncles.*—Length: About 2 to 2.5 cm. Aspect: Arching. Strength: Moderately strong. Texture: Smooth. Color: Greenish pink.

*Reproductive organs.*—Stamens: Stamen number: Eight per flower. Stamen length: About 3 to 3.5 cm. Anther shape: Oblong. Anther color: Dark pink. Pollen amount: Moderate. Pollen color: Light yellow. Pistils: Pistil number: One per flower. Style length: About 5 to 5.5 cm. Style color: Pink. Stigma shape: Ovate, elongated. Stigma color: Dark pink. Ovary color: Light green.

*Fruit.*—Type: Berry. Length: About 1.3 cm. Diameter: About 1 cm. Color: Light purple.

Disease resistance: Plants of the new Fuchsia have not been observed to be resistant to pathogens common to Fuchsias.

Temperature tolerance: Plants of the new Fuchsia have been observed to tolerate low temperatures of 10° C. and high temperatures of 30° C.

Garden performance: Plants of the new Fuchsia have been observed to perform well in the garden and are tolerant to rain and wind.

It is claimed:

1. A new and distinct cultivar of Fuchsia plant named 'Kiewidiv', as illustrated and described.

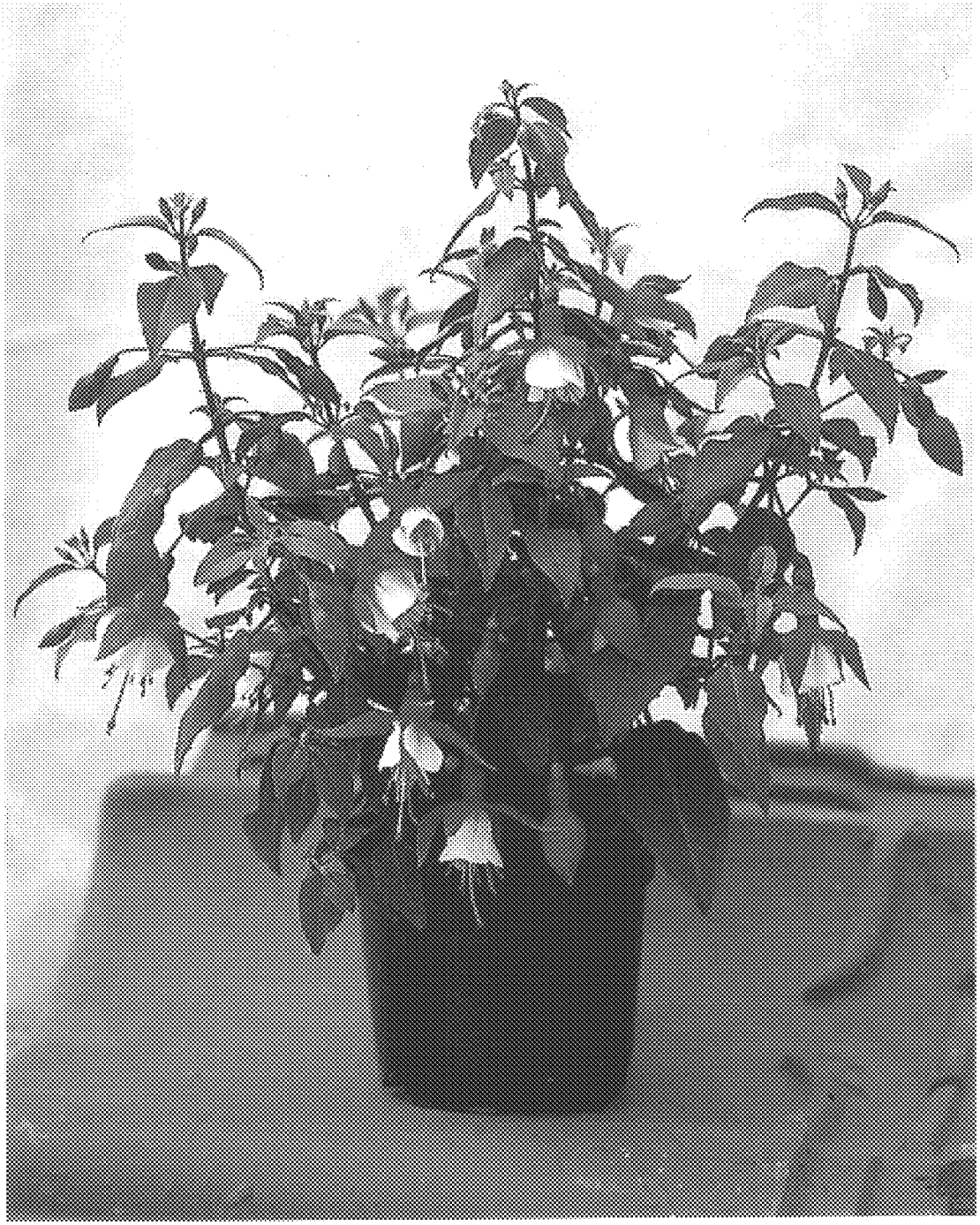

* * * * *